United States Patent
Wang et al.

(10) Patent No.: US 11,459,380 B2
(45) Date of Patent: Oct. 4, 2022

(54) TRANSGLYCOSYLATION OF ENDO-S AND ENDO-S MUTANTS FOR ANTIBODY GLYCOSYLATION REMODELING

(71) Applicant: UNIVERSITY OF MARYLAND, COLLEGE PARK, Waldorf, MD (US)

(72) Inventors: Lai-Xi Wang, Ellicott City, MD (US); Xin Tong, College Park, MD (US); Tiezheng Li, Columbia, MD (US)

(73) Assignee: University of Maryland, College Park, College Park, MD (US)

( * ) Notice: Subject to any disclaimer, the term of this patent is extended or adjusted under 35 U.S.C. 154(b) by 475 days.

(21) Appl. No.: 16/022,978

(22) Filed: Jun. 29, 2018

(65) Prior Publication Data

US 2019/0002542 A1 Jan. 3, 2019

Related U.S. Application Data

(60) Provisional application No. 62/526,635, filed on Jun. 29, 2017.

(51) Int. Cl.

| | |
|---|---|
| *C07K 16/18* | (2006.01) |
| *C07K 1/04* | (2006.01) |
| *C07K 1/36* | (2006.01) |
| *C07K 1/02* | (2006.01) |
| *C07K 1/107* | (2006.01) |
| *A61K 47/61* | (2017.01) |
| *C12N 1/20* | (2006.01) |
| *A61K 47/54* | (2017.01) |
| *A61K 47/68* | (2017.01) |
| *C07K 16/28* | (2006.01) |
| *C07K 16/32* | (2006.01) |
| *C12N 9/24* | (2006.01) |
| *C12P 21/00* | (2006.01) |
| *C12R 1/46* | (2006.01) |
| *A61K 9/00* | (2006.01) |

(52) U.S. Cl.
CPC ............ *C07K 16/18* (2013.01); *A61K 47/549* (2017.08); *A61K 47/61* (2017.08); *A61K 47/6803* (2017.08); *C07K 1/02* (2013.01); *C07K 1/045* (2013.01); *C07K 1/1077* (2013.01); *C07K 1/36* (2013.01); *C07K 16/2887* (2013.01); *C07K 16/32* (2013.01); *C12N 1/205* (2021.05); *C12N 9/2402* (2013.01); *C12P 21/005* (2013.01); *A61K 9/0019* (2013.01); *C07K 2317/10* (2013.01); *C07K 2317/24* (2013.01); *C07K 2317/41* (2013.01); *C12R 2001/46* (2021.05); *C12Y 302/01096* (2013.01)

(58) Field of Classification Search
None
See application file for complete search history.

(56) References Cited

U.S. PATENT DOCUMENTS

| | | | |
|---|---|---|---|
| 7,524,821 B2 | 4/2009 | Wang et al. | |
| 7,556,809 B2 | 7/2009 | Wang | |
| 7,604,804 B2 | 10/2009 | Wang et al. | |
| 7,728,106 B2 | 6/2010 | Wang | |
| 7,807,405 B2 | 10/2010 | Wang | |
| 8,354,247 B2 | 1/2013 | Wang | |
| 8,900,826 B2 | 12/2014 | Wang | |
| 9,175,326 B2 | 11/2015 | Wang | |
| 9,434,786 B2 | 9/2016 | Wang et al. | |
| 9,605,050 B2 | 3/2017 | Wang | |
| 9,845,360 B2 | 12/2017 | Wang et al. | |
| 9,850,473 B2 | 12/2017 | Wang | |
| 2015/0087814 A1 | 3/2015 | Wang et al. | |
| 2015/0176045 A1 | 6/2015 | Marcel et al. | |
| 2019/0002542 A1 | 1/2019 | Wang et al. | |
| 2019/0002945 A1 | 1/2019 | Wang et al. | |

FOREIGN PATENT DOCUMENTS

| WO | WO-2013120066 A1 * | 8/2013 | ......... C07K 14/4725 |
|---|---|---|---|
| WO | WO2015057066 | 4/2015 | |

OTHER PUBLICATIONS

Goodfellow, Jonathan J., et al. "An endoglycosidase with alternative glycan specificity allows broadened glycoprotein remodelling." Journal of the American Chemical Society 134.19 (2012): 8030-8033. (Year: 2012).*

Sun, Qing, et al. "Hybrid-and complex-type N-glycans are not essential for Newcastle disease virus infection and fusion of host cells." Glycobiology 22.3 (2012): 369-378. (Year: 2012).*

Sjögren, Jonathan, et al. "EndoS and EndoS2 hydrolyze Fc-glycans on therapeutic antibodies with different glycoform selectivity and can be used for rapid quantification of high-mannose glycans." Glycobiology 25.10 (2015): 1053-1063. (Year: 2015).*

Adams, G. P. et al. Monoclonal antibody therapy of cancer. *Nat. Biotechnol.* (2005) 23:1147-1157.

Aggarwal, S. R. A survey of breakthrough therapy designations. *Nat. Biotechnol.* (2014) 32:323-330.

Amin, M.N. et al. Synthetic glycopeptides reveal the glycan specificity of HIV-neutralizing antibodies, *Nat Chem Biol*, (2013), 9:521-526.

(Continued)

*Primary Examiner* — Robert J Yamasaki
(74) *Attorney, Agent, or Firm* — Carter, Deluca & Farrell LLP; George Likourezos

(57) ABSTRACT

The present invention provides for a one-pot enzymatic approach which does not require removal of the enzyme and purification of the intermediate after deglycosylation step, and the Endo-S treatment is able to do both deglycosylation and transglycosylation. The one-pot strategy of the present invention enables chemoenzymatic synthesis of an azido-tagged N-glycoform of monocloncal antibodies which could be further modified through orthogonal chemical ligation for various applications.

5 Claims, 8 Drawing Sheets

Specification includes a Sequence Listing.

(56) References Cited

OTHER PUBLICATIONS

Anthony, R. M. et al. Recapitulation of IVIG anti-inflammatory activity with a recombinant IgG Fc. *Science* (2008) 320:373-376.

Collin, M. et al. "EndoS, a novel secreted protein from *Streptococcus pyogenes* with endoglycosidase activity on human IgG", *The EMBO Journal*, (2001) 20(12), : 3046-3055.

Dalziel, M. et al. Emerging principles for the therapeutic exploitation of glycosylation. *Science* (2014) 343:1235681.

Danby, P.M. et al. Advances in Enzymatic Glycoside Synthesis, *ACS Chem Biol.* (2016); 11:1784-1794.

Giddens, J. P. et al. Chemoenzymatic Glyco-engineering of Monoclonal Antibodies. *Methods Mol. Biol.* (2015) 1321:375-387.

Goodfellow, J.J. et al. An endoglycosidase with alternative glycan specificity allows broadened glycoprotein remodeling, *J Am Chem Soc*, (2012), 134:8030-8033.

Huang, W. et al. Glycosynthases enable a highly efficient chemoenzymatic synthesis of N-glycoproteins carrying intact natural N-glycans. *J. Am. Chem. Soc.* (2009) 131:2214-2223.

Huang, W. et al. Arthrobacter endobeta-N-acetylglucosaminidase shows transglycosylation activity on complex-type N-glycan oxazolines: one-pot conversion of ribonuclease B to sialylated ribonuclease C. *ChemBioChem* (2010) 11:1350-1355.

Huang, W. et al. Chemoenzymatic glycoengineering of intact IgG antibodies for gain of functions. *J. Am. Chem. Soc.* (2012) 134:12308-12318.

Illidge, T. et al. Update on obinutuzumab in the treatment of B-cell malignancies. *Expert Opin. Biol. Ther.* (2014) 14:1507-1517.

Jefferis, R. Glycosylation as a strategy to improve antibody-based therapeutics. *Nat. Rev.Drug Discov.* (2009) 8:226-234.

Kaneko, Y. et al. Anti-inflammatory activity of immunoglobulin G resulting from Fc sialylation. *Science* (2006) 313:670-673.

Kurogochi, M. et al. Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities. *PLoS One* (2015) 10:e0132848.

Le, N. P. et al. Immune recruitment or suppression by glycan engineering of endogenous and therapeutic antibodies. *Biochim. Biophys. Acta*. (2016) 1860:1655-1668.

Li, T. et al. Glycosynthase mutants of endoglycosidase S2 show potent transglycosylation activity and remarkably relaxed substrate specificity for antibody glycosylation remodeling, *Journal of Biological Chemistry*, (2016) 291(32):16508-16518.

Li, T. et al. Modulating IgG effector function by Fc glycan engineering. *Proc Natl Acad Sci U S A*, (2017); 114:3485-3490.

Lin, C. W. et al. A common glycan structure on immunoglobulin G for enhancement of effector functions. *Proc. Natl. Acad. Sci. USA* (2015) 112:10611-10616.

Liu, R. et al. Evaluation of a glycoengineered monoclonal antibody via LC-MS analysis in combination with multiple enzymatic digestion, *MAbs* (2016) 8:340-346.

Niwa, R. et al. Defucosylated chimeric anti-CC chemokine receptor 4 IgG1 with enhanced antibody-dependent cellular cytotoxicity shows potent therapeutic activity to T-cell leukemia and lymphoma. *Cancer Res*. (2004) 64:2127-2133.

Ochiai, W. et al. Expeditious chemoenzymatic synthesis of homogeneous N-glycoproteins carrying defined oligosaccharide ligands, *J Am Chem Soc*, (2008) 130: 13790-13803.

Parsons, T. B. Optimal Synthetic Glycosylation of a Therapeutic Antibody. *Angew. Chem. Int. Ed*. (2016) 55:23 61-2367.

Pincetic, A, Type I and type II Fc receptors regulate innate and adaptive immunity. *Nat Immunol.* (2014); 15:707-716.

Quast, I. et al. Sialylation of IgG Fc domain impairs complement-dependent cytotoxicity. *J. Clin. Invest*. (2015) 125:4160-4170.

Schwab, I. et al. Broad requirement for terminal sialic acid residues and FcgammaRIIB for the preventive and therapeutic activity of intravenous immunoglobulins in vivo, *Eur. J. Immunol*. (2014) 44:1444-1453.

Sjorgren, J. et al. EndoS2 is a unique and conserved enzyme of serotype M49 group A *Streptococcus* that hydrolyses N-linked glycans on IgG and alpha1-acid glycoprotein. *Biochem. J*. (2013) 455:107-118.

Sjorgren, J. et al. EndoS and EndoS2 hydrolyze Fc-glycans on therapeutic antibodies with different glycoform selectivity and can be used for rapid quantification of high-mannose glycans. *Glycobiology* (2015) 25:1053-1063.

Van de Bovenkamp, F. S. et al . The Emerging Importance of IgG Fab Glycosylation in Immunity. *J. Immunol*. (2016) 196:1435-1441.

Wang, L-X. et al. Emerging technologies for making glycan-defined glycoproteins. *ACS Chem Biol*. (2012);7:110-122.

Wang, L. X. et al. Chemical and chemoenzymatic synthesis of glycoproteins for deciphering functions. *Chem. Biol*. (2014) 21:51-66.

Washburn, N. et al. Controlled tetra-Fc sialylation of IVIg results in a drug candidate with consistent enhanced anti-inflammatory activity. *Proc. Natl. Acad. Sci. USA* (2015) 112:E1297-1306.

\* cited by examiner (A)

(B)

Scheme 3

TRANSGLYCOSYLATION OF ENDO-S AND ENDO-S MUTANTS FOR ANTIBODY GLYCOSYLATION REMODELING

CROSS-REFERENCE TO RELATED APPLICATION

This application claims priority to U.S. Provisional Application No. 62/526,635 filed on Jun. 29, 2017, the contents of which are incorporated by reference herein for all purposes.

GOVERNMENT RIGHTS IN INVENTION

This invention was made with government support under R01GM096973B awarded by the NIH. The government has certain rights in the invention.

BACKGROUND OF THE INVENTION

Field of the Invention

The invention relates to glycoprotein synthesis, and more particularly, to the use of a one-pot enzymatic approach which does not require removal of the enzyme and purification of the intermediate after deglycosylation step, and the Endo-S treatment is able to do both deglycosylation and transglycosylation. The one-pot strategy uses an Endo S enzyme, an Endo-β-N-acetylglucosaminidase from *Streptococcus pyogenes*.

Description of the Related Art

Therapeutic monoclonal antibodies are an important class of therapeutic proteins that are widely used for the treatment of human diseases, including cancer, inflammatory disorders, and infectious diseases.[1,2] All types of antibodies (IgG, IgA, IgD, IgM, and IgE) are glycosylated at the Fc domain. In the case of the IgG type antibodies, the Fc glycosylation at the conserved N297 glycosylation site has been shown to play a crucial role in modulating antibody's effector functions.[3,4,5,6] Moreover, the fine structures of the Fc glycans can sometimes dictate the fate of a given antibody.[3,7,8] For example, it has been well documented that removal of the core fucose from the Fc glycans of rituximab, a therapeutic monoclonal antibody, significantly enhances its antibody-dependent cellular cytotoxicity (ADCC), mainly through an enhanced binding to the FcγIIIa receptor on the effector cells, resulting in its improved therapeutic efficacy in anti-cancer therapy.[9,10] On the other hand, the terminal α-2,6-sialylation of intravenous immunoglobulin (IVIG) has been shown to be important for IVIG's anti-inflammatory activity.[11,12,13,14] Thus controlling Fc glycosylation to the correct state is critically important for producing effective therapeutic antibodies. Nevertheless, recombinant antibodies are usually produced as mixtures of heterogeneous glycoforms that have the same protein backbone but differ in the Fc glycans attached, from which pure homogeneous glycoforms are difficult to separate.

To address this problem, systems have been developed using an in vitro chemoenzymatic glycan remodeling approach for engineering Fc glycosylation, which involves two key steps: an endoglycosidase-catalyzed deglycosylation to remove the heterogeneous Fc N-glycans, and a subsequent enzymatic transfer of a pre-assembled N-glycan from the activated N-glycan oxazoline to constitute the desired homogeneous antibody glycoforms.[15,16] Two bacterial endoglycosidases, the Endo-S from *Streptococcus pyogenes* and the Endo-S2 from the *Streptococcus pyogenes* of serotype M49 have been found to be highly active and specific for Fc deglycosylation of intact IgG antibodies.[17,18,19] It has been previously demonstrated that Endo-S possesses transglycosylation activity and that glycosynthases mutants, such as EndoS-D233Q, can be generated which lack the hydrolysis activity on antibody glycoforms, but are able to use the highly active glycan oxazoline for transglycosylation to give homogeneous glycoforms.[20] More recently, this glycosynthase approach has been extended to the Endo-S2 and have generated new glycosynthases that could use all major types of N-glycan oxazolines for transglycosylation.[21] Several groups have used the glycosynthase approach for the synthesis of various homogeneous glycoforms of antibodies for structural and functional studies.[8,22,23,24,25,26,27] Despite these successes, one drawback of this glycan remodeling method is that the wild-type enzyme (Endo-S or Endo-S2) used for the deglycosylation needs to be separated from the reaction mixture after the deglycosylation step in order to avoid hydrolyzing the final product, and the second step requires a glycosynthase mutant for transglycosylation, followed by another purification step.

Thus, it would be advantageous to develop a method for glycan remodeling wherein the deglycosylation enzyme does not have to be removed during the process.

SUMMARY OF THE INVENTION

The present invention provides for the use of the wild-type Endo-S showing promiscuous activity on both the hybrid and high-mannose type glycan oxazolines for transglycosylation with marginal hydrolytic activity on the product glycoforms. The unique substrate specificity of Endo-S, coupled with its highly efficient hydrolysis on the complex-type N-glycans, permitted the development of an efficient, one-pot glycosylation remodeling method for therapeutic antibodies. Importantly, the one-pot enzymatic approach of the present invention does not require removal of the Endo-S enzyme and purification of the intermediate after deglycosylation step, and the Endo-S treatment is able to do both deglycosylation and transglycosylation. The one-pot strategy of the present invention enables chemoenzymatic synthesis of an azido-tagged N-glycoform of an antibody which could be further modified through orthogonal chemical ligation for various applications.

In one aspect, the present invention provides for a method for glycosylation remodeling method for a therapeutic antibody, the method comprising:
a. providing a single container;
b. introducing into the container a core fucosylated or non-fucosylated antibody or Fc fragment thereof comprising Fc N-glycans;
c. introducing into the container and treating the core fucosylated antibody or Fc fragment with Endo-S enzyme having an amino acid sequence of SEQ ID NO: 1 to yield a Asn-linked GlcNAc moiety; and
d. introducing into the container a high-mannose or hybrid glycan oxazoline for attaching to the Asn-linked GlcNAc moiety in the presence of the Endo-S, thereby adding the high-mannose or hybrid glycan oxazoline to provide a remodeled glycosylated therapeutic antibody.

The high-mannose or hybrid glycan oxazoline has a predetermined oligosaccharide component with a defined number and type of sugar residues and with specific linkage types.

In a further aspect, the present invention relates to a single pot remodeling method of a core fucosylated or nonfucosylated IgG or IgG-Fc fragment with an oligosaccharide having a predetermined oligosaccharide component with a defined number and type of sugar residues and with specific linkage types, the method comprising:

providing a single pot
providing and introducing into the single pot a core fucosylated or nonfucosylated IgG or IgG-Fc fragment obtained from natural or recombinant sources carrying heterogeneous N-glycans;
treating the natural or recombinant IgG or IgG-Fc fragment with an wild type *Streptococcus pyogenes* Endo-S having an amino acid sequence of SEQ ID NO: 1 to hydrolyze the bond between the two GlcNAc residues positioned closest to the peptide domain thereby forming a deglycosylated protein carrying a core fucosylated or nonfucosylated GlcNAc-acceptor; and
attaching the predetermined oligosaccharide component to the GlcNAc-acceptor to reconstitute the natural beta-1,4-glycosidic bond through transglycosylation with the *Streptococcus pyogenes* Endo-S already in the single pot, thereby adding the predetermined oligosaccharide component to remodel the core fucosylated or nonfucosylated IgG or IgG-Fc fragment.

Applicable oligosaccharide oxazolines include, but not limited to, high-mannose type, hybrid type, sialoglycan oxazoline and complex type N-glycan, as well as their selectively modified derivatives such as those with specific tags. Preferably, penta-, hexyl-, hepta-, octyl-, nona-, deca-, or undeca-saccharide oxazolines are utilized as donor substrates for a highly efficient chemoenzymatic synthesis of homogeneous core fucosylated or nonfucosylated IgG antibodies and IgG-Fc fragments.

Further is was found that chemical modification at the outer mannose moieties was found to be effective and resisted hydrolysis by the wild type Endo S enzyme, thus a Man3 glycan oxazoline can be protected by the addition of an extra moiety such as N3 to resist hydrolysis by the wild type Endo-S enzyme.

In yet another aspect, the present invention provides a single pot method of remodeling an intravenous immunoglobulin (IVIG) exhibiting Fc-sialylated glycoforms, the method comprising:
a. providing a single pot;
b. providing and introducing into the single pot an IVIG carrying Fc N-glycans;
c. introducing a wild *Streptococcus pyogenes* Endo-S(SEQ ID NO: 1) enzyme into the single pot;
d. Fc deglycosylating the Fc N-glycans using the wild *Streptococcus pyogenes* Endo-S(SEQ ID NO: 1) to form GlcNAc-acceptors; wherein the GlcNAc-acceptors are positioned on the Fc region of the IVIG and the GlcNAc-acceptors are either fucosylated or nonfucosylated; and
e. transglycosylating the GlcNAc-acceptors with a sialoglycan oxazoline having a predetermined number of sugar residues under the catalysis of the wild Endo S enzyme to form a sialylated IVIG, wherein the wild Endo S enzyme remains in the single pot during the entire process.

In yet another aspect, the present invention relates to a single pot method to synthesize a modified antibody or fragment thereof, the method comprising;
providing a single pot;
providing and introducing into the single pot a naturally existing IgG antibody, a recombinant antibody or a Fc domain carrying Fc N-glycans as precursors;
introducing the wild *Streptococcus pyogenes* Endo-S (SEQ ID NO: 1) for Fc deglycosylating the Fc domain to form a GlcNAc-acceptor; wherein the GlcNAc-acceptor is positioned on the Fc region of the antibody and the GlcNAc-acceptor is either core fucosylated or nonfucosylated; and
transglycosylating the GlcNAc-acceptor in the naturally existing IgG antibody, the recombinant antibody or the Fc domain with an oligosaccharide oxazoline or a sialoglycan oxazoline having a predetermined number of sugar residues under the catalysis of the wild *Streptococcus pyogenes* Endo-S(SEQ ID NO: 1) to form the modified antibody with the predetermined number of sugar residues, wherein the wild *Streptococcus pyogenes* Endo-S (SEQ ID NO: 1) enzyme remains in the single pot during the entire process.

Other aspects, features and embodiments of the invention will be more fully apparent from the ensuing disclosure and appended claims.

DETAILED DESCRIPTION OF THE PRESENT INVENTION

Figure 1:
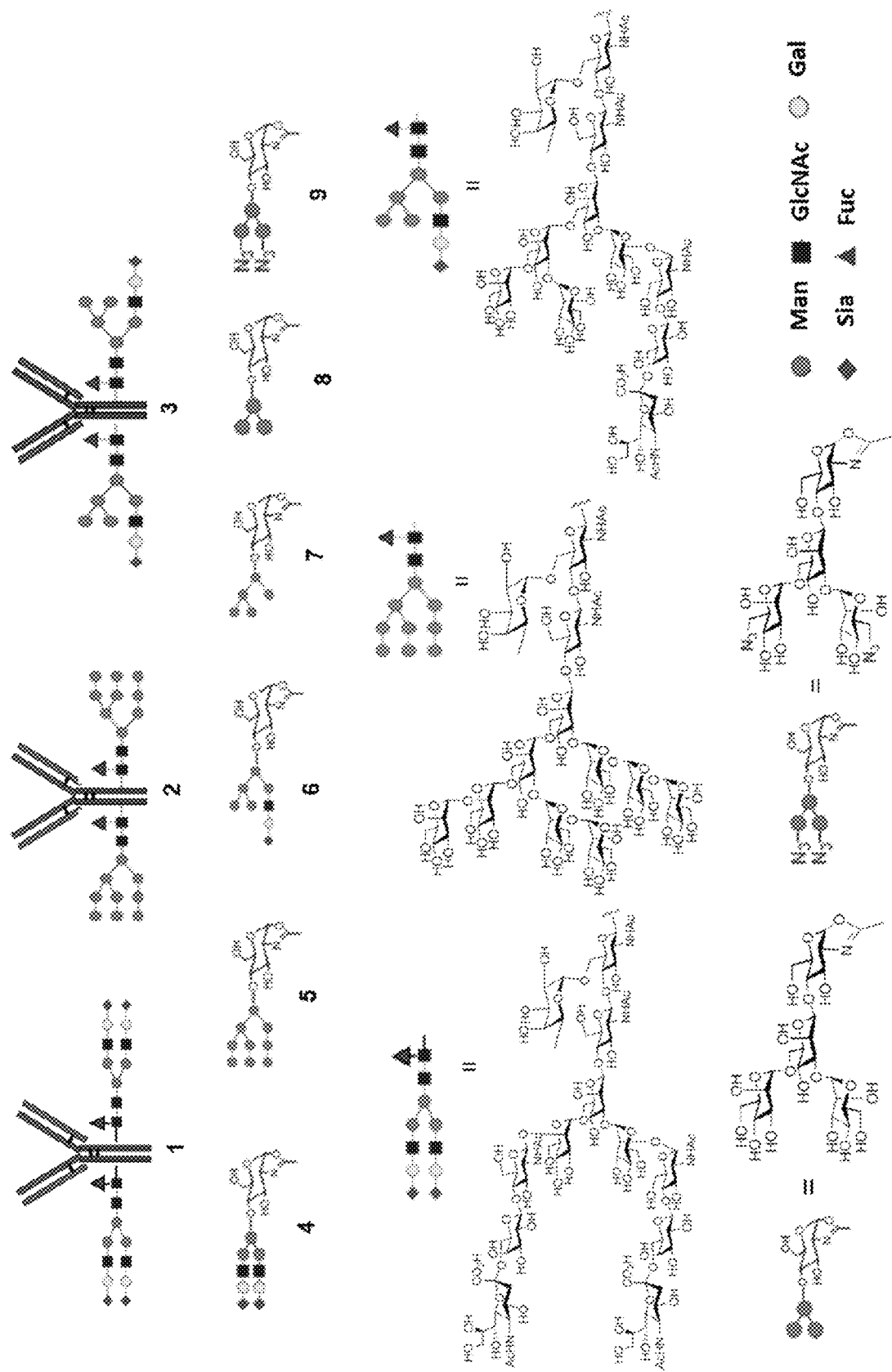
FIG. 1 shows structures of rituximab glycoforms and various N-glycan oxazolines used for the assessment of Endo-S activity.

The present invention provides a facile, one-pot enzymatic glycan remodeling of antibody rituximab to produce homogeneous high-mannose and hybrid type antibody glycoforms is described. This method was based on the unique substrate specificity of the endoglycosidase S (Endo-S) from *Streptococcus pyogenes*. While Endo-S efficiently hydrolyzes the bi-antennary complex type IgG Fc N-glycans, it was found that Endo-S did not hydrolyze the "ground state" high-mannose or hybrid glycoforms, and only slowly hydrolyzed the highly activated high-mannose or hybrid N-glycan oxazolines. Moreover, it was found that wild-type Endo-S could efficiently use high-mannose or hybrid glycan oxazolines for transglycosylation without product hydrolysis. The combination of the remarkable difference in substrate specificity of Endo-S allows the deglycosylation of a heterogeneous antibody and the transglycosylation with glycan oxazoline to take place in one-pot without the need of isolating the deglycosylated intermediate or changing the enzyme to afford the high-mannose type, hybrid type, and some selectively modified truncated form of antibody glycoforms.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

It is understood that aspects of the present invention described herein include "consisting" and/or "consisting essentially of" aspects.

Definitions

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or non-oxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, D or L-fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core-fucosylated glycoproteins or nonfucosylated glycoproteins wherein the oligosaccharide component comprises at least 75%, more preferably at least 90%, and most preferably at least 95% of the same number and types of sugar residues.

As used herein, "protein" or "glycoprotein" is interchangeable with the terms peptide and glycopeptide.

As used herein, "homology" refers to amino acid sequence having substantial identity or similarity between two polypeptides and having at least 85%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

It is envisioned that many different fucosylated glycoproteins and nonfucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Fucosylated and nonfucosylated glycoproteins are important classes of biomolecules that play crucial roles in many biological events such as cell adhesion, tumor metastasis, pathogen infection, and immune response. As indicated previously herein, a major problem in structural and functional studies of fucosylated or nonfucosylated glycoproteins is their structural microheterogeneity. Natural and recombinant fucosylated or nonfucosylated glycoproteins are typically produced as a mixture of glycoforms that differ only in the structure of the pendent oligosaccharides.

The remodeled glycoproteins, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The fucosylated and nonfucosylated glycoproteins, produced according to the methods described herein, can be used for diagnosis and therapeutics. Approximately two-thirds of therapeutic proteins used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials and the Endo-S2 mutants of the present invention are able to transglycosylate fucosylated and nonfucosylated natural and recombinant glycoproteins without the negative aspects of hydrolysis.

The features and advantages of the present invention are more fully shown by the following non-limiting examples.

Examples

Comparative Analysis of the Endo-S-Catalyzed Hydrolysis of Different Rituximab Glycoforms and Synthetic N-Glycan Oxazolines Previously, Collin and co-workers have reported that Endo-S and Endo-S2 hydrolyze Fc-glycans of therapeutic antibodies with different substrate specificity. While Endo-S2 can release all three major types of N-glycans from the Fc domain of several therapeutic antibodies including cetuximab, Endo-S is only efficient for releasing bi-antennary complex type N-glycans from the antibodies.[19] To further confirm the substrate selectivity of the wild-type Endo-S, side-by-side comparative analysis of Endo-S-catalyzed hydrolysis reactions was performed for the selected homogeneous glycoforms of rituximab, as well as various synthetic N-glycan oxazolines (FIG. 1).

Figure 2:
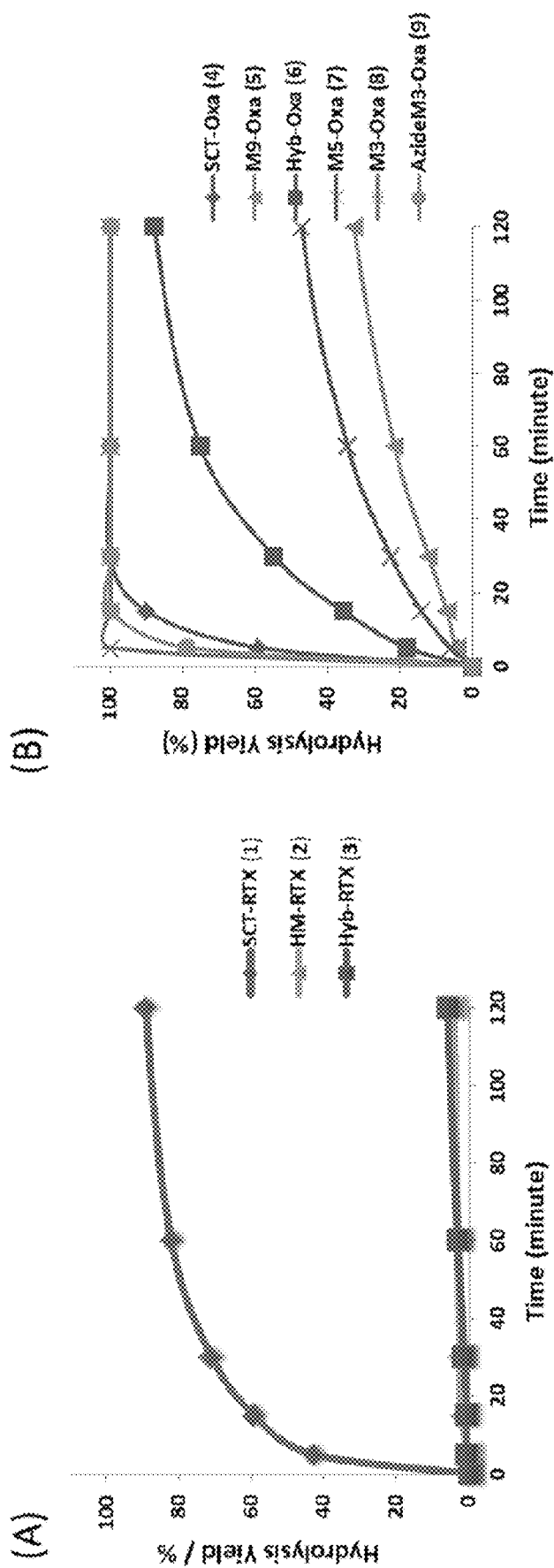
FIG. 2 shows the hydrolytic activity of Endo-S WT on different rituximab glycoforms and N-glycan oxazolines. A) Comparison of the hydrolytic activity of Endo-S WT towards the complex (1), hybrid (2) and high-mannose (3) type glycoforms of rituximab; B) Comparison of the hydrolytic activity of Endo-S WT towards various N-glycan oxazolines. The results shown here are representative of three independently conducted experiments.

Three different homogeneous glycoforms of rituximab were tested, namely, the sialylated complex type (1), the high-mannose (Man9GlcNAc2) type (2), and the hybrid type (3) (FIG. 1). These homogeneous glycoforms (1-3) were synthesized following recently published method, using the Endo-S2 glycosynthase mutant (EndoS2-D184M) as a key enzyme for transglycosylation.[21] The enzymatic reaction was monitored by LC-ESI-MS analysis. It was found that Endo-S could hydrolyze the bi-antennary complex type glycoform of rituximab (1) fast, resulting in over 90% hydrolysis within 2 h under the reaction condition. However, only marginal hydrolysis (less than 5%) of the high-mannose and hybrid glycoforms (2 and 3) was observed under the same reaction condition (FIG. 2A). A prolonged (overnight) incubation resulted in about 10% hydrolysis of the high mannose glycoform (2) and approximate 15% of the hybrid glycoform (3), respectively (data not shown). These data confirm that the high-mannose and hybrid type Fc glycoforms of antibodies are largely resistant to Endo-S-catalyzed hydrolysis although residual hydrolytic activity was detected, and the bi-antennary complex type glycoform is an excellent substrate for the wild-type Endo-S.

Next, the Endo-S WT catalyzed hydrolysis of various synthetic glycan oxazolines were compared. Synthetic glycan oxazolines, the mimics of the oxazolinium intermediate during the endoglycosidase-catalyzed reaction in a substrate-assisted mechanism, are the key donor substrates for the endoglycosidase-catalyzed transglycosylation used for glycoprotein remodeling.[15, 16, 28] Thus, it is important to know whether the glycan oxazolines will be hydrolyzed and how fast they will be hydrolyzed by the enzyme of interest. Various glycan oxazolines were incubated with Endo-S WT in PBS buffer, and the hydrolysis products (free glycans) were monitored and quantitated by HPAEC-PAD (the high performance anion exchange chromatography coupled with pulsed amperometric electrochemical detection). As shown in FIG. 2B, the complex type glycan oxazoline (4)[29] was rapidly hydrolyzed by Endo-S WT. In contrast, the high-mannose type N-glycans oxazolines, including the Man9 oxazoline (M9-Oxa 5)[30] and the Man5 glycan oxazoline (Man5-Oxa 7),[31] were shown to be rather resistant to Endo-S hydrolysis. The hybrid type oxazoline (Hyb-Oxa 6)[21] showed moderate hydrolysis by Endo-S WT. Surprisingly, the Man3 oxazoline (M3-Oxa 8),[32] corresponding to the shared N-glycan core, was hydrolyzed even faster than the bi-antennary complex type N-glycan oxazoline (SCT-Oxa 4) by Endo-S (FIG. 2B). However, chemical modification at the two outer mannose moieties led to reduction of the enzymatic hydrolysis, as demonstrated by the azide-Man3 glycan oxazoline (AzideM3-Oxa 9)[32] (FIG. 2B). These results clearly indicate that wild-type Endo-S possesses distinct enzymatic activities towards different glycan oxazolines, as well as different glycoforms of antibodies.

Figure 3:
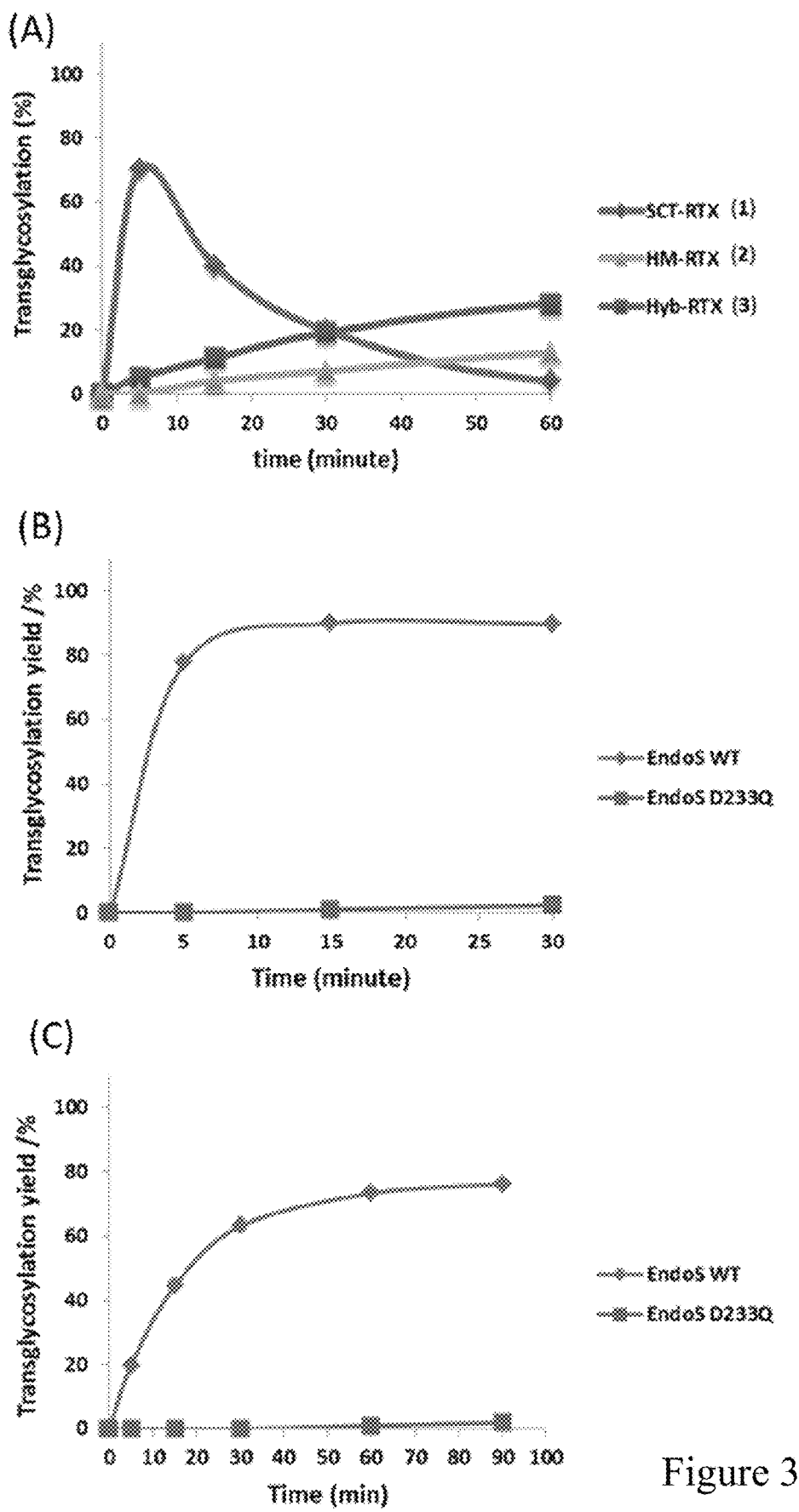
FIG. 3 shows Endo-S and EndoS-D233Q mutant catalyzed transglycosylation with different N-glycan oxazolines. A) Comparison of the transglycosylation activity of Endo-S WT with complex type (SCT-Oxa 4), high-mannose type (HM-Oxa 5), and hybrid type (Hyb-Oxa 6) glycan oxazolines; B) Comparison of the transglycosylation activity of Endo-S WT and Endo-S D233Q mutant with the high mannose-type oxazoline (HM-Oxa 5); C) Comparison of the transglycosylation activity of Endo-S WT and Endo-S D233Q mutant with the hybrid-type oxazoline (Hyb-Oxa 6). The results shown here are representative of three independently conducted experiments.

Endo-S-Catalyzed Transglycosylation of Deglycosylated Rituximab with Different N-Glycan Oxazolines The distinct substrate specificity of Endo-S towards different antibody glycoforms and N-glycan oxazolines provide an incentive to examine the wild-type Endo-S-catalyzed transglycosylation with the three major Fc N-glycans oxazolines, complex (SCT-Oxa 4), Man9 (HM-Oxa 5), and Hybrid (Hyb-Oxa 6), to the deglycosylated rituximab (Fucα1,6GlcNAc-rituximab, 10) (Scheme 1). The acceptor Fucα1,6GlcNAc-rituximab (10) was prepared by deglycosylation of rituximab with Endo-S, following our previously published procedure.[20] It was found that the wild-type Endo-S showed a significant transglycosylation activity with the complex type N-glycan oxazoline (4) to form the transglycosylation product (1) (FIG. 3). However, the product was quickly hydrolyzed by the enzyme, as the resultant complex type glycoform turned out to be an excellent substrate for Endo-S-catalyzed hydrolysis. This result was consistent with previous observation.[20] It was also observed that, under the same condition, wild-type Endo-S was also able to transfer the high-mannose glycan oxazoline (5) and hybrid glycan oxazoline (6), but at a much lower reaction rate than that with the complex type glycan oxazoline (4) (FIG. 3).

Nevertheless, since the transglycosylation products (2 and 3) were largely resistant to Endo-S-catalyzed hydrolysis, the transglycosylation products could thus be accumulated. The present inventors previous generated novel Endo-S mutants, including EndoS-D233Q, which are glycosynthases that can use glycan oxazolines for transglycosylation but lack the activity to hydrolyze the product.[20] The EndoS-D233Q mutant was efficient for transferring complex type N-glycan oxazolines to the deglycosylated antibody, however, it was not clear how the glycosynthase mutant would act on the high-mannose and hybrid type N-glycan oxazolines. Thus EndoS-D233Q with oxazolines 5 and 6 was tested for transglycosylation. Surprisingly, it was found that the Endo-S mutant, EndoS-D233Q, was unable to act on either the high-mannose glycan oxazoline (5) or the hybrid glycan oxazoline (6) for transglycosylation with the Fucα1, 6GlcNAc-rituximab (10), while under the same condition the wild-type Endo-S could achieve over 85% transglycosylation to form the corresponding antibody glycoforms (FIG. 3B and FIG. 3C). One explanation is that, in comparison with the wild-type enzyme, the D233Q mutation could reduce both the hydrolysis and transglycosylation activities of the enzyme, thus, resulting in decreased efficiency towards the less favorable glycan oxazoline substrates, while it was still active enough towards the complex type N-glycan oxazoline (4), as shown in the previous publication.[20] These new experimental data suggest that the wild-type Endo-S is complementary to the mutant Endo-S in terms of their substrate specificities, and the Endo-S WT will be particularly useful for the synthesis of antibodies with high-mannose and hybrid glycoforms, which could not be achieved by the previously reported Endo-S mutants.

One-Pot N-Glycosylation Remodeling of Commercial Rituximab Via Wild-Type Endo-S

Figure 4:
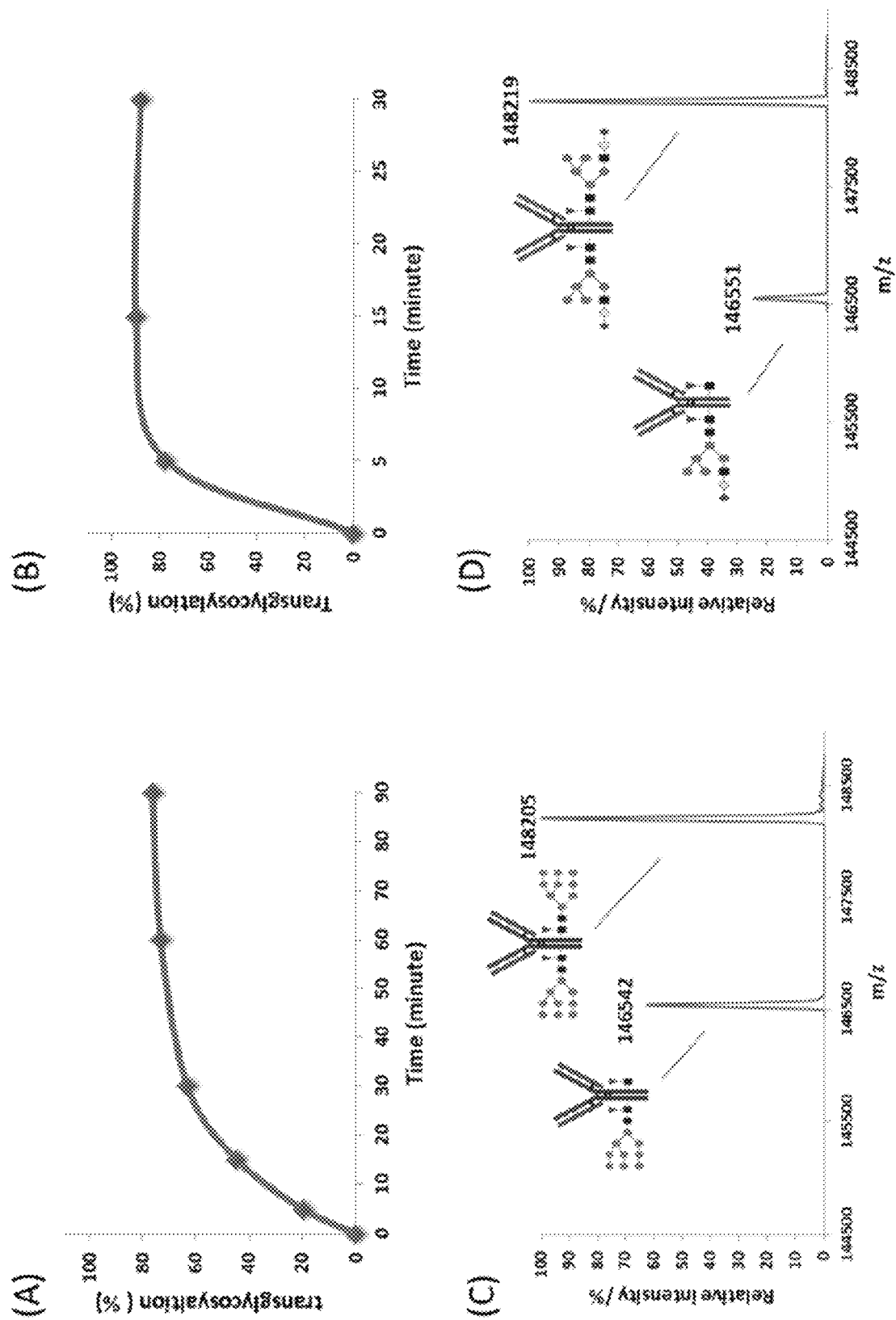
FIG. 4 shows Endo-S catalyzed one-pot glycan remodeling of rituximab with high-mannose and hybrid glycan oxazolines. A) Enzymatic remodeling with high-mannose N-glycan oxazoline (5); B) enzymatic remodeling with hybrid N-glycan oxazoline (6); C) LC-ESI-MS profile of the transglycosylation products from the enzymatic remodeling with high-mannose N-glycan oxazoline (5); D) LC-ESI-MS profile of the transglycosylation products from the enzymatic remodeling with the hybrid N-glycan oxazoline (6). The results shown here are representative of two independently conducted experiments.

The potent transglycosylation activity of Endo-S WT with the hybrid and high-mannose type oxazolines, together with its efficient hydrolysis of the complex-type N-glycans from the commercial antibody rituximab, caused the present inventors to examine the possibility of remodeling antibody glycosylation in a one-pot fashion (Scheme 2). Thus, a mixture of the commercial rituximab, glycan oxazoline (5 or 6), and wild-type Endo-S was incubated in a buffer at room temperature and the reaction was monitored by LC-ESI-MS analysis. As expected, the Endo-S-catalyzed deglycosylation of rituximab took place rapidly and was completed within 5 min under the reaction condition, even before any significant transglycosyaltion could occur (data not shown). Then the transglycosylation product (2 or 3) was steadily formed over the time without apparent hydrolysis, reaching about 80% within 2 h (FIGS. 4A and B). As the IgG monoclonal antibody (rituximab) is a dimer consisting of two heavy chains and two light chains in which only the Fc domain of the heavy chain is glycosylated, the transglycosylation yield was calculated by the following equation: yield (%)=fully transglycosylated rituximab/(deglycosylated rituximab+partially transglycosylated rituximab+fully transglycosylated rituximab)×100. The relative intensity of the deglycosylated, partially transglycosylated, and fully transglycosylated rituximab species in the LC-MS analysis was estimated for the calculation. This offered a quick estimate of the transglycosyaltion yield but did not imply an accurate quantification.

It was also observed that the transglycosylation with the hybrid type glycan oxazoline (6) went faster than that of the high-mannose type glycan oxazoline (5) under the same condition. The LC-ESI-MS profiles of the intact antibodies after transglycosylation were shown in FIGS. 4C and D. The experimental data indicated that the free N-glycans in the medium released from the deglycosylation step did not interfere with the transglycosylation step, and the one pot approach was able to transform the heterogeneous rituximab into high-mannose or hybrid type glycoforms without the need of separating the deglycosylated intermediate or changing the enzyme. It should be pointed out that this transformation could be optimized to push the reaction to completion by adding more glycan oxazoline and/or enzyme with prolonged incubation time.

Figure 5:
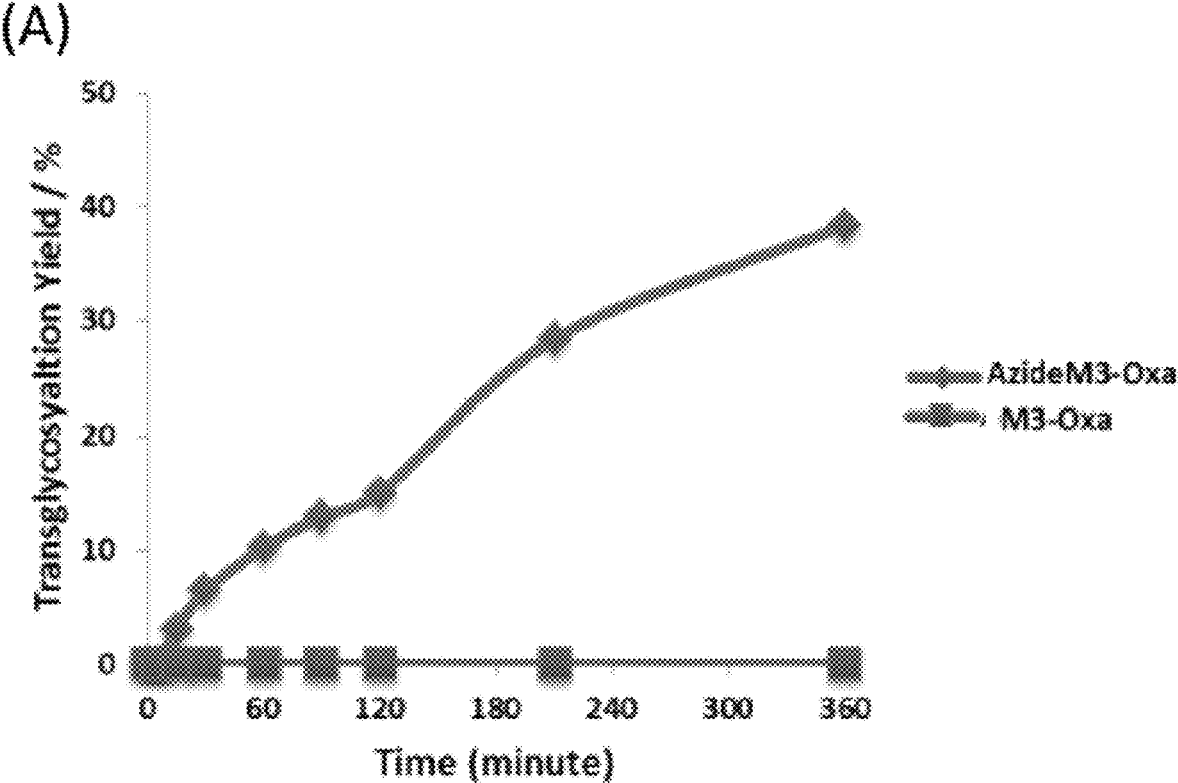
FIG. 5 show Endo-S catalyzed one-pot glycan remodeling of rituximab with Man3 glycan oxazoline and azide-Man3 glycan oxazoline. A) the time course of reactions with the Man3 glycan oxazoline (Man3-Oxa 8) and the azide-Man3 glycan oxazoline (azideM3-Oxa 9); B) the LC-ESI-MS profile of the transglycosylation products from the enzymatic remodeling with the Man3 glycan oxazoline (Man3-Oxa 8). The results shown here are representative of two independently conducted experiments.
Figure 5:
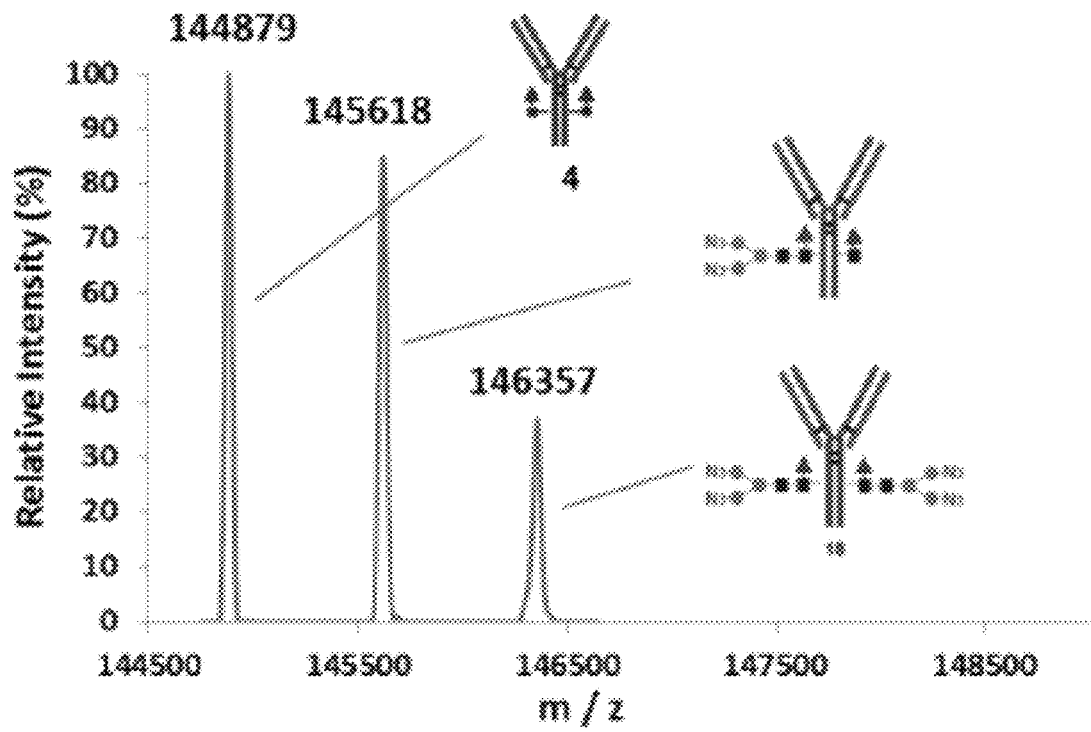
Figure 6:
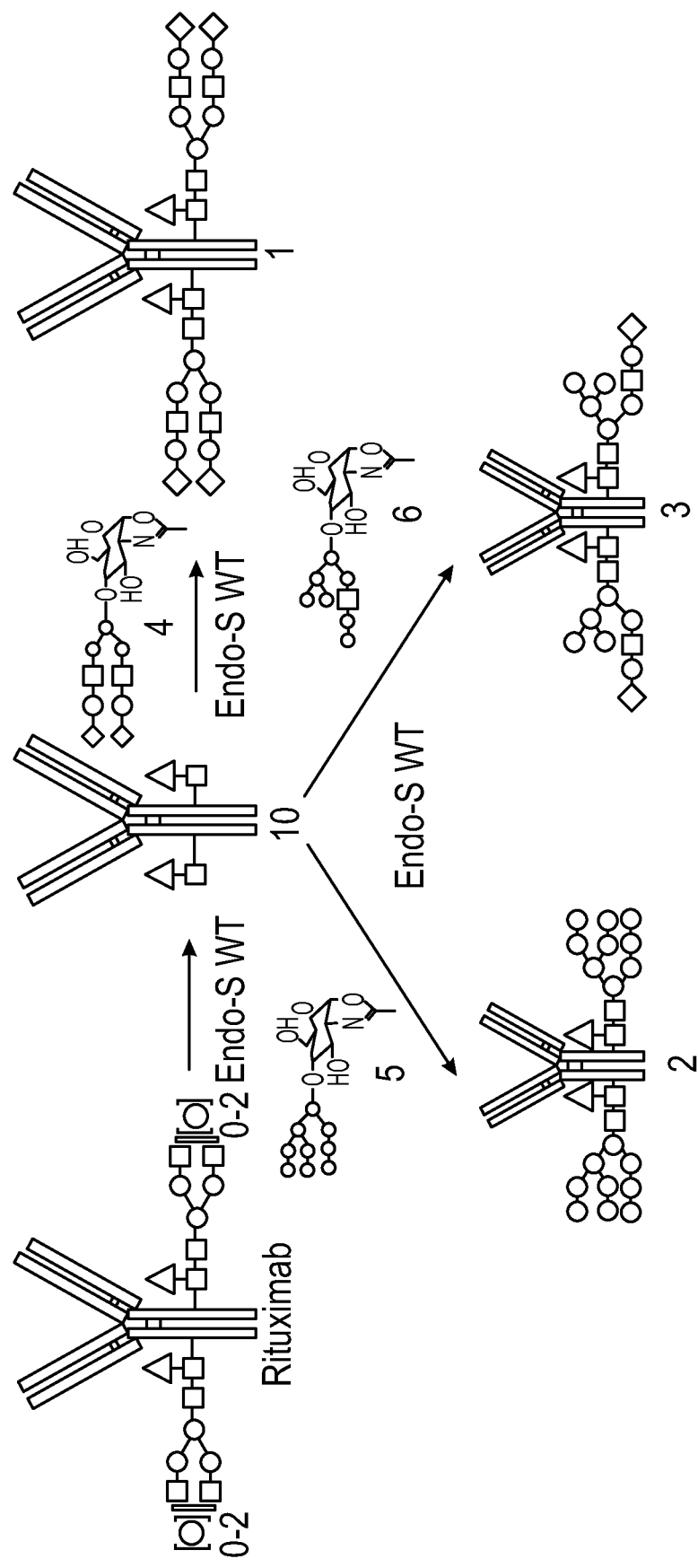
FIG. 6 shows Scheme 1: Transglycosylation activity of Endo-S with different types of N-glycan oxazolines.
Figure 7:
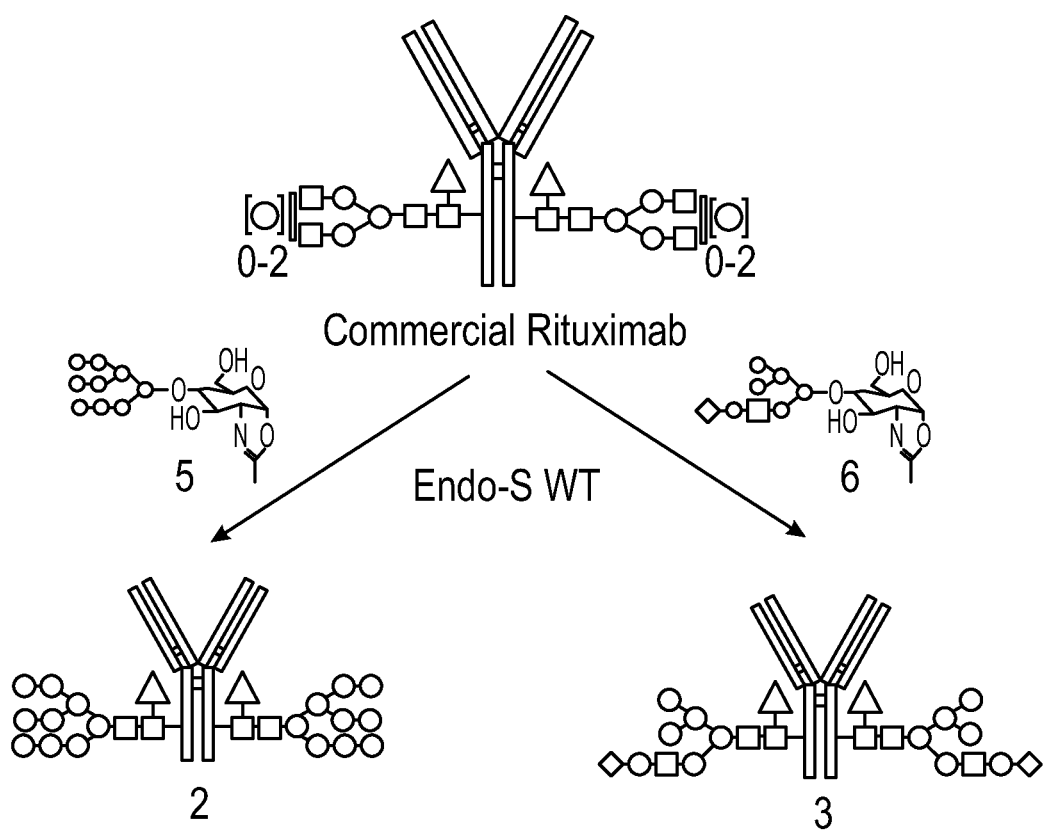
FIG. 7 shows Scheme 2: One-pot enzymatic glycan remodeling of commercial rituximab by Endo-S with high-mannose and hybrid type N-glycan oxazolines.
Figure 8:
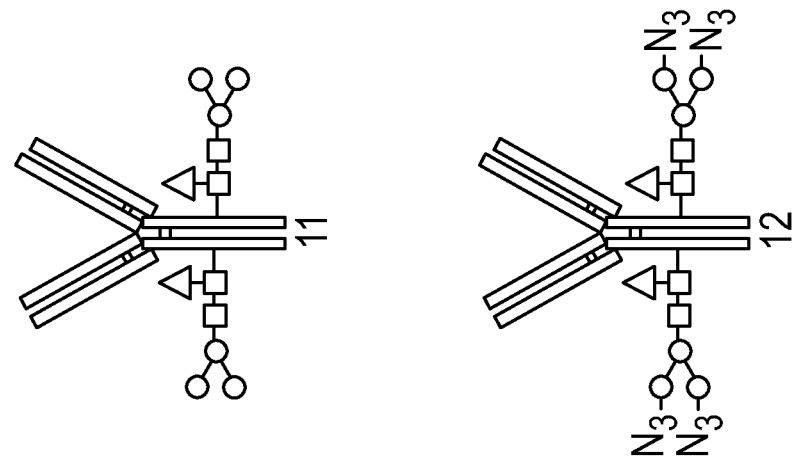
FIG. 8 shows Scheme 3: One-pot enzymatic glycan remodeling of commercial rituximab by Endo-S with azide-modified Man3 glycan oxazoline.
Figure 8:
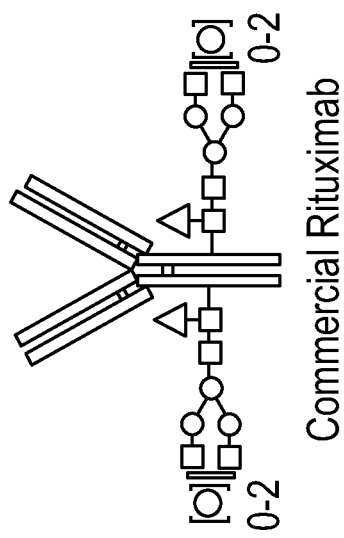
Figure 8:
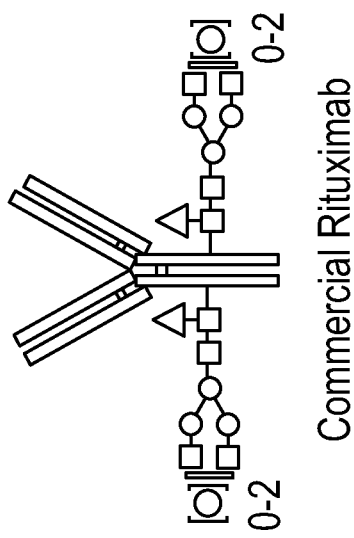

One-Pot Glycan Remodeling of Commercial Rituximab with the Azido-Tagged Azide-Man3GlcNAc oxazoline by the wild-type Endo-S In addition to the hybrid and high mannose type N-glycans, the present inventors also tested the ability of Endo-S to act on the azido-tagged azide-Man3GlcNAc oxazoline (AzideM3-Oxa, 9) for Fc glycan remodeling of rituximab in a one-pot manner (Scheme 3). Following the same one-pot reaction protocol described above, it was found that the conversion took place relatively slowly, but the transglycosylation product, the azide-tagged glycoform of rituximab (11) was formed steadily. Within 6 h, nearly 40% conversion was achieved (FIG. 5). The Man3 glycan oxazoline (M3-Oxa 8) was also tested. Interestingly, only marginal amount of transglycosylation product was detected by LC-MS analysis in the case of using the Man3 glycan oxazoline (8) (FIG. 5A). This result is consistent with previous comparative study on Man3 glycan oxazoline (8) with Endo-S D233Q mutant and the wild-type Endo-S, where only transition formation of the transglycosylation product was observed by SDS-PAGE analysis when the wild-type Endo-S was used, whereas high-yield conversion was achieved using the EndoS-D233Q mutant.[20]

Indeed, as shown in the oxazoline hydrolysis experiment described above (FIG. 2), the Man3-glycan oxazoline (8) was also hydrolyzed very rapidly by the wild-type Endo-S. In addition, the transglycosylation product was also hydrolyzed quickly by the wild-type Endo-S. Thus it was not a surprise that only transitional transglycosylation product was detected during the reaction. It should be pointed out that Davis and co-workers previously reported the Endo-S-catalyzed transglycosylation with Man3 glycan oxazoline on the deglycosylated IgG antibody, but no detailed quantitative characterization of the transglycosylation product was reported except MS analysis of the released N-glycans.[33] In the present case of the azide-Man3 glycan oxazoline (9), the present enzymatic glycan oxazoline hydrolysis experiment showed that the chemical modification increased to some extent its resistance towards Endo-S-catalyzed hydrolysis (FIG. 2), which could partially explain the moderate transglycosylation yield. It is expected that the one-pot enzymatic glycan remodeling method might be extended to other site-selective modified glycan oxazolines to synthesize selectively tagged glycoforms of various antibodies.

Conclusion

The present invention demonstrates that wild-type Endo-S possesses remarkably different hydrolysis and transglycosylation activity on different N-glycan oxazolines and glycoforms of antibodies, using therapeutic monoclonal antibody rituximab as a model system. The potent activity to deglycosylate the recombinant complex type glycoforms of antibodies, the promiscuous transglycosylation activity on the high-mannose and hybrid type N-glycan oxazolines, and yet the lack of hydrolysis activity on the "ground-state" high-mannose and hybrid type glycoforms has enabled an efficient one-pot enzymatic glycan remodeling of heterogeneous glycoforms of rituximab to produce homogenous high-mannose or hybrid type glycoforms, without the need of intermediate separation and enzyme switching. This one-pot enzymatic glycan remodeling method should be also applicable to other therapeutic antibodies for obtaining specific glycoforms of antibodies for various applications.

Experimental Procedures

Monoclonal antibody, rituximab, was purchased from Genentech Inc., (South San Francisco, Calif.). Complex-type (SCT) sialoglycan oxazoline (4) and high mannose-type (HM) oxazoline (5) were harvested and synthesized from egg yolk and soybean flour, respectively, following previously described methods.[29, 30] The hybrid-type (Hyb) oxazoline (6) was converted from Man5GlcNAc (7) via a multi-step enzymatic treatment using a series of previously described enzymes, including the β-1,2-GlcNAc transferase (GnT1), β-1,4-galactosyltransferase, and sialyltransferase.[21] The Man3 (M3-Oxa 8) and Azide-tagged Man3 (AizdeM3-Oxa 9) oxazolines were synthesized according to a previously publication.[32]

Expression and Purification of Recombinant Endo-S WT and Endo-SD233Q

The pGEX plasmid vector encoding the wild-type Endo-S(SEQ ID NO 1) was a gift from Dr. M. Collin (Lund University, Sweden). Site-directed mutagenesis was conducted as described in the previous publication to generate Endo-S D233Q mutant DNA (SEQ ID NO. 2). The plasmid DNA encoding both the wild-type Endo-S and the Endo-S D233Q mutant was transformed in E. coli BL21 (DE3) cells for overexpression. For purification of the enzyme, the transformed cells were grown in 1 L 2YT media with 100 µg/mL Carbenicillin added. Cells were incubated at 37° C. and induced with 0.5 mM isopropyl β-d-1-thiogalactopyranoside (IPTG) when the cell density reached an OD600 of 0.8-1.0. The induced cells were incubated at 20° C. overnight and harvested by centrifugation. The cell lysates were collected after treating with bacterial cell lysis buffer (Gold Biotechnology, Inc.) following manufacturer's instructions. The GST-tagged proteins were purified using the GST resin batch method (Thermo). The purified proteins were diluted into PBS at pH 7.4 after buffer exchange using Amicon ultra filtration units (10 kDa, Millipore). The purity of Endo-S proteins was over 90% on SDS-PAGE and the final concentration was recorded on a NanoDrop 2000c at absorbance 280 nm.

Liquid Chromatography Mass Spectrometry (LC-ESI-MS) Analysis

Antibody N-glycoforms were studied using an Exactive Plus Orbitrap instrument equipped with a HPLC system and an ESI source. The capillary temperature and the spray voltage were set up according to previous publications. Approximately 25 µL of intact rituximab solution was injected and separated via a Waters XBridge™ BEH300 C4 column (3.5 2.1×50 mm) at a flow rate of 0.4 mL/min. The program includes a 9 min linear gradient of 5-90% MeCN containing 0.1% formic acid. The starting material deglycosylated rituximab (m/z 144879) and different transglycosylation products were measured using selected ion monitoring (SIM). The signal intensities of the target ions were optimized by automatic tuning function and the same optimized conditions were used in all LC-MS quantifications. The MagTran Software (Amgen) was used to analyze the data from the exported chromatogram results. An average of scans was analyzed through deconvolution to give a spectrum list for each analyzed sample. Integration of the deconvoluted spectrum shows the relative abundance of the analyzed ions. Total peak intensities within 0.7 mass units surrounding the center of the target ion peak were used to determine the ratio of the starting material and the product species. This relative ratio can then be used to calculate the reaction yield of each hydrolysis and transglycosylation reaction with the concentration of the starting material known.

HPAEC-PAD Analysis of Glycans and Oxazolines

High-performance anion-exchange chromatography coupled with pulsed amperometric detection (HPAEC-PAD) was conducted on a DIONEX chromatography system (DIONEX Corporation, Sunnyvale, Calif.) using an anion exchange column (CarboPac PA200, 3×250 mm). The sample was delivered with a mobile phase consisting of deionized water (eluent A), 0.2 M NaOH (eluent B), 0.1 M NaOH (eluent C) and 0.1 M NaOH with 0.25 M NaoAc (eluent D). The program for the complex and hybrid type glycans and oxazolines used a gradient as follows: 0 min, 0% eluent A, 0% eluent B, 100% eluent C and 0% eluent D; 5.0 min, 0% eluent A, 0% eluent B, 100% eluent C and 0% eluent D; and 25.0 min, 0% eluent A, 0% eluent B, 60% eluent C and 40% eluent D at a flow rate of 1.0 mL/min. The program for oligomannose type glycans and oxazolines (Mang, Man5, Man3 and Azide-Man3) were analyzed using a different program: 0 min, 0% eluent A, 0% eluent B, 100% eluent C and 0% eluent D; 5.0 min, 0% eluent A, 0% eluent B, 100% eluent C and 0% eluent D; and 25.0 min, 0% eluent A, 0% eluent B, 80% eluent C and 20% eluent D with a flow rate of 1.0 mL/min. The relative abundance of each glycan and oxazoline was calculated from the integrated spectrum.

Comparison of the Hydrolytic Activity of Endo-S WT Towards Different Rituximab Glycoforms The rituximab glycoforms, SCT-RTX 1, HM-RTX 2 and Hyb-RTX 3 were synthesized according to the previously published protocol.[21] In three parallel reactions, each of the three N-glycoforms (0.01 mg, 6.9 μM) was incubated with Endo-S WT (5 μg/mL) at 30° C. in 20 μl of PBS buffer (pH 7.4) for a given amount of time. The reaction was quenched by adding 20 μl of 0.1% formic acid and the sample was placed at −20° C. The hydrolysis yield was measured by calculating the ratio of the hydrolyzed product versus the starting material using LC-ESI-MS as shown above.

Comparison of the Hydrolytic Activity of Endo-S WT Towards Various Oxazolines

In parallel reactions, SCT-Oxa 4, HM-Oxa 5, Hyb-Oxa 6, M5-Oxa 7, M3-Oxa 8 and AzideM3-Oxa 9 oxazolines (1 mM) was incubated with Endo-S WT (50 μg/ml) at 30° C. in 25 μl of PBS buffer (pH 7.4). Aliquots of reaction mixture (1 μl) was sampled at the same time intervals and diluted in 100 mM NaOH solution to quench the reaction. All reactions were monitored by HPAEC-PAD and the relative percentage of the hydrolyzed oxazoline (free glycan) was quantified from the integrated spectrum as detailed in previous sections.

Evaluation of the Transglycosylation Activity of Endo-S WT Towards the Deglycosylated Rituximab Using SCT-Oxa 4, HM-Oxa 5 and Hyb-Oxa 6 as Glycosyl Donors The ability of Endo-S WT to transfer three different N-glycan oxazolines SCT-Oxa 4, HM-Oxa 5 and Hyb-Oxa 6 to the deglycosylated rituximab[10] in a conventional two-step transglycosylation reaction was compared under the same condition. First, the commercial rituximab underwent deglycosylation by incubation with a catalytic amount of Endo-S WT (10 μg/ml) at 30° C. for a short period of time. Once complete deglycosylation was confirmed, the deglycosylated rituximab was subsequently purified through Protein-A chromatography for further transglycosylation. The following reaction was performed using the deglycosylated rituximab 10 (10 mg/mL) as the glycosyl acceptor and N-glycan oxazolines as glycosyl donors with a catalytic amount of Endo-S WT (50 μg/ml) at 30° C. in 20 μl of PBS buffer (pH 7.4). The molar ratio of the donor substrate to the glycosyl acceptor was 40:1.

Evaluation of Transglycosylation Activity of Endo-S WT and Endo-S D233Q Towards the Deglycosylated Rituximab Using HM-Oxa 5 and Hyb-Oxa 6 as Glycosyl Donor The transglycosylation efficiency of Endo-S WT and Endo-S D233Q towards the deglycosylated rituximab was compared separately for HM-Oxa 5 and Hyb-Oxa 6. The deglycosylated rituximab was prepared as mentioned above. For reaction with either oxazoline, the deglycosylated rituximab 10 (10 mg/mL) was incubated with each enzyme (500 μg/ml) at 30° C. in 20 μl of PBS buffer (pH 7.4). The molar ratio of the donor substrate to the glycosyl acceptor was also 40:1. The transglycosylation products were analyzed and quantified as mentioned previously.

Transglycosylation of Commercial Rituximab with Hyb-Oxa and HM-Oxa by Endo-S WT in a One-Pot Manner Commercial Rituximab (0.1 mg, 69 μM) was dissolved in PBS buffer (pH 7.4) and was mixed with 40 equivalents of hybrid and high mannose oxazolines HM-oxa 5 (2.8 mM) and Hyb-oxa 6 (2.8 mM), respectively. The reaction was initiated by adding a catalytic amount of Endo-S WT (500 μg/ml) and incubated in PBS at 30° C. (pH 7.4). For product quantification, the concentration of the product glycoform carrying two N-glycans, 148205 for HM-RTX and 148219 for Hyb-RTX (deconvoluted mass), were counted twice as each antibody molecule carries two glycosylation sites. The N-glycoform carrying only one N-glycan for each oxazoline was only counted once as the product formed. The same quantification method using LC-ESI-MS was used for the similar experiments conducted in this present invention.

Transglycosylation of Commercial Rituximab with M3-Oxa and AzideM3-Oxa by the Endo-S WT in a One-Pot Fashion Commercial Rituximab (0.1 mg, 69 μM) was incubated in PBS at 30° C. (pH 7.4) with 40 equivalents of oxazolines M3-Oxa 8 (2.8 mM) and AzideM3-Oxa 9 (2.8 mM), respectively. To initiate the reaction, a fixed amount of Endo-S WT (500 μg/ml) was added into the reaction mixture at t=0 min. The reactions with M3-Oxa and AzideM3-Oxa were maintained for a prolonged period of time to allow the accumulation of the transglycosylation product. Additional 40 equivalents of oxazolines were added to each reaction at t=120 min. Transglycosylation with AzideM3-Oxa 9 showed three species at 144879 (starting material), 145618 (product with a single glycan attached) and 146357 (product with two glycans attached). The reaction yield was quantified as described above.

The references cited herein are incorporated by reference herein for all purposes.

1. Adams G P, Weiner L M. Monoclonal antibody therapy of cancer. *Nat Biotechnol.* 2005; 23:1147-1157.
2. Aggarwal S R. A survey of breakthrough therapy designations. *Nat Biotechnol.* 2014; 32:323-330.
3. Jefferis R. Glycosylation as a strategy to improve antibody-based therapeutics. *Nat Rev Drug Discov.* 2009; 8:226-234.
4. Dalziel M, Crispin M, Scanlan C N, Zitzmann N, Dwek R A. Emerging principles for the therapeutic exploitation of glycosylation. *Science.* 2014; 343:1235681.
5. van de Bovenkamp F S, Hafkenscheid L, Rispens T, Rombouts Y. The Emerging Importance of IgG Fab Glycosylation in Immunity. *J Immunol.* 2016; 196:1435-1441.
6. Le N P, Bowden T A, Struwe W B, Crispin M. Immune recruitment or suppression by glycan engineering of endogenous and therapeutic antibodies. *Biochim Biophys Acta.* 2016; 1860:1655-1668.
7. Pincetic A, Bournazos S, DiLillo D J, et al. Type I and type I I Fc receptors regulate innate and adaptive immunity. *Nat Immunol.* 2014; 15:707-716.
8. Li T, DiLillo D J, Bournazos S, Giddens J P, Ravetch J V, Wang L X. Modulating IgG effector function by Fc glycan engineering. *Proc Natl Acad Sci USA.* 2017; 114:3485-3490.
9. Niwa R, Shoji-Hosaka E, Sakurada M, et al. Defucosylated chimeric anti-C C chemokine receptor 4 IgG1 with enhanced antibody-dependent cellular cytotoxicity shows potent therapeutic activity to T-cell leukemia and lymphoma. *Cancer Res.* 2004; 64:2127-2133.
10. Illidge T, Cheadle E J, Donaghy C, Honeychurch J. Update on obinutuzumab in the treatment of B-cell malignancies. *Expert Opin Biol Ther.* 2014; 14:1507-1517.
11. Kaneko Y, Nimmerjahn F, Ravetch J V. Anti-inflammatory activity of immunoglobulin G resulting from Fc sialylation. *Science.* 2006; 313:670-673.
12. Anthony R M, Nimmerjahn F, Ashline D J, Reinhold V N, Paulson J C, Ravetch J V. Recapitulation of IVIG anti-inflammatory activity with a recombinant IgG Fc. *Science.* 2008; 320:373-376.
13. Schwab I, Mihai S, Seeling M, Kasperkiewicz M, Ludwig R J, Nimmerjahn F. Broad requirement for terminal sialic acid residues and FcgammaRIIB for the preventive and therapeutic activity of intravenous immunoglobulins in vivo. *Eur J Immunol.* 2014; 44:1444-1453.
14. Washburn N, Schwab I, Ortiz D, et al. Controlled tetra-Fc sialylation of IVIg results in a drug candidate with consistent enhanced anti-inflammatory activity. *Proc Natl Acad Sci USA.* 2015; 112:E1297-1306.
15. Wang L X, Lomino J V. Emerging technologies for making glycaN-defined glycoproteins. *ACS Chem Biol.* 2012; 7:110-122.
16. Wang L X, Amin M N. Chemical and chemoenzymatic synthesis of glycoproteins for deciphering functions. *Chem Biol.* 2014; 21:51-66.
17. Collin M, Olsen A. EndoS, a novel secreted protein from *Streptococcus pyogenes* with endoglycosidase activity on human IgG. *EMBO J* 2001; 20:3046-3055.
18. Sjogren J, Struwe W B, Cosgrave E F, et al. EndoS2 is a unique and conserved enzyme of serotype M49 group A *Streptococcus* that hydrolyses N-linked glycans on IgG and alpha1-acid glycoprotein. *Biochem J.* 2013; 455:107-118.
19. Sjogren J, Cosgrave E F, Allhorn M, et al. EndoS and EndoS2 hydrolyze Fc-glycans on therapeutic antibodies with different glycoform selectivity and can be used for rapid quantification of high-mannose glycans. *Glycobiology.* 2015; 25:1053-1063.
20. Huang W, Giddens J, Fan S Q, Toonstra C, Wang L X. Chemoenzymatic glycoengineering of intact IgG antibodies for gain of functions. *J Am Chem Soc.* 2012; 134:12308-12318.
21. Li T, Tong X, Yang Q, Giddens J P, Wang L X. Glycosynthase mutants of endoglycosidase S2 show potent transglycosylation activity and remarkably relaxed substrate specificity for antibody glycosylation remodeling. *J Biol Chem.* 2016; 291:16508-16518.
22. Quast I, Keller C W, Maurer M A, et al. Sialylation of IgG Fc domain impairs complement-dependent cytotoxicity. *J Clin Invest.* 2015; 125:4160-4170.
23. Giddens J P, Wang L X. Chemoenzymatic Glycoengineering of Monoclonal Antibodies. *Methods Mol Biol.* 2015; 1321:375-387.
24. Lin C W, Tsai M H, Li S T, et al. A common glycan structure on immunoglobulin G for enhancement of effector functions. *Proc Natl Acad Sci USA.* 2015; 112:10611-10616.
25. Kurogochi M, Mori M, Osumi K, et al. Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities. *PLoS ONE.* 2015; 10:e0132848.
26. Parsons T B, Struwe W B, Gault J, et al. Optimal Synthetic Glycosylation of a Therapeutic Antibody. *Angew Chem Int Ed.* 2016; 55:2361-2367.
27. Liu R, Giddens J, McClung C M, Magnelli P E, Wang L X, Guthrie E P. Evaluation of a glycoengineered monoclonal antibody via L C-M S analysis in combination with multiple enzymatic digestion. *MAbs.* 2016; 8:340-346.
28. Danby P M, Withers S G. Advances in Enzymatic Glycoside Synthesis. *ACS Chem Biol.* 2016; 11:1784-1794.
29. Huang W, Yang Q, Umekawa M, Yamamoto K, Wang L X. Arthrobacter Endobeta-N-acetylglucosaminidase shows transglycosylation activity on complex type N-glycan oxazolines: one-pot conversion of ribonuclease B to sialylated ribonuclease C. *ChemBioChem.* 2010; 11:1350-1355.
30. W. Huang, C. Li, B. Li, et al. Glycosynthases enable a highly efficient chemoenzymatic synthesis of N-glycoproteins carrying intact natural N-glycans, *J Am Chem Soc,* 131 (2009), pp. 2214-2223.
31. M. N. Amin, J. S. McLellan, W. Huang, et al. Synthetic glycopeptides reveal the glycan specificity of HIV-neutralizing antibodies, *Nat Chem Biol,* 9 (2013), pp. 521-526.
32. H. Ochiai, W. Huang, L. X. Wang, Expeditious chemoenzymatic synthesis of homogeneous N-glycoproteins carrying defined oligosaccharide ligands, *J Am Chem Soc,* 130 (2008), pp. 13790-13803.
33. J. J. Goodfellow, K. Baruah, K. Yamamoto, et al., An endoglycosidase with alternative glycan specificity allows broadened glycoprotein remodeling, *J Am Chem Soc,* 134 (2012), pp. 8030-8033.

That which is claimed is:

1. A glycosylation remodeling method for a therapeutic antibody or Fc fragment thereof with a *Streptococcus pyogenes* wild-type endoglycosidase-S (Endo-S), the method comprising:
   providing a single container;
   introducing into the single container the *Streptococcus pyogenes* wild-type Endo-S, a core fucosylated or non-fucosylated antibody or Fc fragment thereof comprising Fc N-glycans including two GlcNAc residues positioned closest to a peptide domain of the antibody;
   introducing into the single container and treating the core fucosylated antibody or non- fucosylated antibody or Fc fragment thereof with the *Streptococcus pyogenes* wild-type Endo-S in the single container and having an amino acid sequence of SEQ ID NO: 1 to hydrolyze a bond between the two GlcNAc residues thereby forming a deglycosylated core fucosylated or nonfucosylated GlcNAc-acceptor to yield an Asn-linked GlcNAc moiety; and
   introducing into the single container a high-mannose oxazoline or hybrid glycan oxazoline having a predetermined oligosaccharide component with a defined number and type of sugar residues and with specific linkage types for reacting with the Asn-linked GlcNAc moiety wherein a transglycosylation step is carried out by the *Streptococcus pyogenes* wild-type Endo-S, thereby adding the predetermined oligosaccharide component to provide a remodeled glycosylated therapeutic antibody or Fc fragment thereof in the single container.

2. The glycosylation remodeling method of claim 1, wherein the *Streptococcus pyogenes* wild-type Endo-S remains in the single container during the glycosylation remodeling method for both deglycosylation and transglycosylati on.

3. The glycosylation remodeling method of claim 1, wherein the high-mannose oxazoline is selected from the group consisting of penta-, hexyl-, hepta-, octyl-, nona-, deca-, and undeca-saccharide oxazolines.

4. The glycosylation remodeling method of claim 3, wherein the hybrid glycan oxazoline comprises a Man3 glycan oxazoline protected by addition of an extra moiety to resist hydrolysis by the *Streptococcus pyogenes* wild-type Endo-S.

5. The glycosylation remodeling method of claim 1, wherein the hybrid glycan oxazoline comprises at least one compound selected from the group consisting of mannose, sialic acid, D-galactose, and L-fucose.

* * * * *

SEQUENCE LISTING

<160> NUMBER OF SEQ ID NOS: 2

<210> SEQ ID NO 1
<211> LENGTH: 995
<212> TYPE: PRT
<213> ORGANISM: Streptococcus pyogenes

<400> SEQUENCE: 1

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365
```

-continued

```
Lys Ala Asn Gly Ile Asn Thr Asp Ile Thr Gly Thr Arg Ala Glu Arg
        370                 375                 380
Tyr Ala Arg Trp Gln Pro Lys Thr Gly Val Lys Gly Gly Ile Phe
385                 390                 395                 400
Ser Tyr Ala Ile Asp Arg Asp Gly Val Ala His Gln Pro Lys Lys Tyr
                    405                 410                 415
Ala Lys Gln Lys Glu Phe Lys Asp Ala Thr Asp Asn Ile Phe His Ser
            420                 425                 430
Asp Tyr Ser Val Ser Lys Ala Leu Lys Thr Val Met Leu Lys Asp Lys
                435                 440                 445
Ser Tyr Asp Leu Ile Asp Glu Lys Asp Phe Pro Asp Lys Ala Leu Arg
            450                 455                 460
Glu Ala Val Met Ala Gln Val Gly Thr Arg Lys Gly Asp Leu Glu Arg
465                 470                 475                 480
Phe Asn Gly Thr Leu Arg Leu Asp Asn Pro Ala Ile Gln Ser Leu Glu
                    485                 490                 495
Gly Leu Asn Lys Phe Lys Lys Leu Ala Gln Leu Asp Leu Ile Gly Leu
                500                 505                 510
Ser Arg Ile Thr Lys Leu Asp Arg Ser Val Leu Pro Ala Asn Met Lys
            515                 520                 525
Pro Gly Lys Asp Thr Leu Glu Thr Val Leu Glu Thr Tyr Lys Lys Asp
            530                 535                 540
Asn Lys Glu Glu Pro Ala Thr Ile Pro Pro Val Ser Leu Lys Val Ser
545                 550                 555                 560
Gly Leu Thr Gly Leu Lys Glu Leu Asp Leu Ser Gly Phe Asp Arg Glu
                    565                 570                 575
Thr Leu Ala Gly Leu Asp Ala Ala Thr Leu Thr Ser Leu Glu Lys Val
                580                 585                 590
Asp Ile Ser Gly Asn Lys Leu Asp Leu Ala Pro Gly Thr Glu Asn Arg
            595                 600                 605
Gln Ile Phe Asp Thr Met Leu Ser Thr Ile Ser Asn His Val Gly Ser
        610                 615                 620
Asn Glu Gln Thr Val Lys Phe Asp Lys Gln Lys Pro Thr Gly His Tyr
625                 630                 635                 640
Pro Asp Thr Tyr Gly Lys Thr Ser Leu Arg Leu Pro Val Ala Asn Glu
                    645                 650                 655
Lys Val Asp Leu Gln Ser Gln Leu Leu Phe Gly Thr Val Thr Asn Gln
                660                 665                 670
Gly Thr Leu Ile Asn Ser Glu Ala Asp Tyr Lys Ala Tyr Gln Asn His
            675                 680                 685
Lys Ile Ala Gly Arg Ser Phe Val Asp Ser Asn Tyr His Tyr Asn Asn
        690                 695                 700
Phe Lys Val Ser Tyr Glu Asn Tyr Thr Val Lys Val Thr Asp Ser Thr
705                 710                 715                 720
Leu Gly Thr Thr Thr Asp Lys Thr Leu Ala Thr Asp Lys Glu Glu Thr
                    725                 730                 735
Tyr Lys Val Asp Phe Phe Ser Pro Ala Asp Lys Thr Lys Ala Val His
                740                 745                 750
Thr Ala Lys Val Ile Val Gly Asp Glu Lys Thr Met Met Val Asn Leu
            755                 760                 765
Ala Glu Gly Ala Thr Val Ile Gly Gly Ser Ala Asp Pro Val Asn Ala
        770                 775                 780
Arg Lys Val Phe Asp Gly Gln Leu Gly Ser Glu Thr Asp Asn Ile Ser
```

```
                785                 790                 795                 800
Leu Gly Trp Asp Ser Lys Gln Ser Ile Ile Phe Lys Leu Lys Glu Asp
                805                 810                 815
Gly Leu Ile Lys His Trp Arg Phe Phe Asn Asp Ser Ala Arg Asn Pro
                820                 825                 830
Glu Thr Thr Asn Lys Pro Ile Gln Glu Ala Ser Leu Gln Ile Phe Asn
                835                 840                 845
Ile Lys Asp Tyr Asn Leu Asp Asn Leu Leu Glu Asn Pro Asn Lys Phe
            850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
                    885                 890                 895
Tyr Trp Arg Val Val Phe Asp Thr Lys Gly Asp Arg Tyr Ser Ser Pro
                900                 905                 910
Val Val Pro Glu Leu Gln Ile Leu Gly Tyr Pro Leu Pro Asn Ala Asp
                915                 920                 925
Thr Ile Met Lys Thr Val Thr Thr Ala Lys Glu Leu Ser Gln Gln Lys
            930                 935                 940
Asp Lys Phe Ser Gln Lys Met Leu Asp Glu Leu Lys Ile Lys Glu Met
945                 950                 955                 960
Ala Leu Glu Thr Ser Leu Asn Ser Lys Ile Phe Asp Val Thr Ala Ile
                965                 970                 975
Asn Ala Asn Ala Gly Val Leu Lys Asp Cys Ile Glu Lys Arg Gln Leu
                980                 985                 990
Leu Lys Lys
        995

<210> SEQ ID NO 2
<211> LENGTH: 995
<212> TYPE: PRT
<213> ORGANISM: Artificial Sequence
<220> FEATURE:
<223> OTHER INFORMATION: Synthetic Construct

<400> SEQUENCE: 2

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Val Gln Lys Gly Leu Pro
            35                  40                  45
Ser Ile Asp Ser Leu His Tyr Leu Ser Glu Asn Ser Lys Lys Glu Phe
        50                  55                  60
Lys Glu Glu Leu Ser Lys Ala Gly Gln Glu Ser Gln Lys Val Lys Glu
65                  70                  75                  80
Ile Leu Ala Lys Ala Gln Gln Ala Asp Lys Gln Ala Gln Glu Leu Ala
                85                  90                  95
Lys Met Lys Ile Pro Glu Lys Ile Pro Met Lys Pro Leu His Gly Pro
                100                 105                 110
Leu Tyr Gly Gly Tyr Phe Arg Thr Trp His Asp Lys Thr Ser Asp Pro
            115                 120                 125
Thr Glu Lys Asp Lys Val Asn Ser Met Gly Glu Leu Pro Lys Glu Val
        130                 135                 140
Asp Leu Ala Phe Ile Phe His Asp Trp Thr Lys Asp Tyr Ser Leu Phe
```

```
            145                 150                 155                 160
Trp Lys Glu Leu Ala Thr Lys His Val Pro Lys Leu Asn Lys Gln Gly
                165                 170                 175
Thr Arg Val Ile Arg Thr Ile Pro Trp Arg Phe Leu Ala Gly Gly Asp
                180                 185                 190
Asn Ser Gly Ile Ala Glu Asp Thr Ser Lys Tyr Pro Asn Thr Pro Glu
                195                 200                 205
Gly Asn Lys Ala Leu Ala Lys Ala Ile Val Asp Glu Tyr Val Tyr Lys
    210                 215                 220
Tyr Asn Leu Asp Gly Leu Asp Val Gln Val Glu His Asp Ser Ile Pro
225                 230                 235                 240
Lys Val Asp Lys Lys Glu Asp Thr Ala Gly Val Glu Arg Ser Ile Gln
                245                 250                 255
Val Phe Glu Glu Ile Gly Lys Leu Ile Gly Pro Lys Gly Val Asp Lys
                260                 265                 270
Ser Arg Leu Phe Ile Met Asp Ser Thr Tyr Met Ala Asp Lys Asn Pro
                275                 280                 285
Leu Ile Glu Arg Gly Ala Pro Tyr Ile Asn Leu Leu Leu Val Gln Val
    290                 295                 300
Tyr Gly Ser Gln Gly Glu Lys Gly Gly Trp Glu Pro Val Ser Asn Arg
305                 310                 315                 320
Pro Glu Lys Thr Met Glu Glu Arg Trp Gln Gly Tyr Ser Lys Tyr Ile
                325                 330                 335
Arg Pro Glu Gln Tyr Met Ile Gly Phe Ser Phe Tyr Glu Glu Asn Ala
                340                 345                 350
Gln Glu Gly Asn Leu Trp Tyr Asp Ile Asn Ser Arg Lys Asp Glu Asp
                355                 360                 365
Lys Ala Asn Gly Ile Asn Thr Asp Ile Thr Gly Thr Arg Ala Glu Arg
    370                 375                 380
Tyr Ala Arg Trp Gln Pro Lys Thr Gly Gly Val Lys Gly Gly Ile Phe
385                 390                 395                 400
Ser Tyr Ala Ile Asp Arg Asp Gly Val Ala His Gln Pro Lys Lys Tyr
                405                 410                 415
Ala Lys Gln Lys Glu Phe Lys Asp Ala Thr Asp Asn Ile Phe His Ser
                420                 425                 430
Asp Tyr Ser Val Ser Lys Ala Leu Lys Thr Val Met Leu Lys Asp Lys
                435                 440                 445
Ser Tyr Asp Leu Ile Asp Glu Lys Asp Phe Pro Asp Lys Ala Leu Arg
    450                 455                 460
Glu Ala Val Met Ala Gln Val Gly Thr Arg Lys Gly Asp Leu Glu Arg
465                 470                 475                 480
Phe Asn Gly Thr Leu Arg Leu Asp Asn Pro Ala Ile Gln Ser Leu Glu
                485                 490                 495
Gly Leu Asn Lys Phe Lys Lys Leu Ala Gln Leu Asp Leu Ile Gly Leu
                500                 505                 510
Ser Arg Ile Thr Lys Leu Asp Arg Ser Val Leu Pro Ala Asn Met Lys
                515                 520                 525
Pro Gly Lys Asp Thr Leu Glu Thr Val Leu Glu Thr Tyr Lys Lys Asp
    530                 535                 540
Asn Lys Glu Glu Pro Ala Thr Ile Pro Pro Val Ser Leu Lys Val Ser
545                 550                 555                 560
Gly Leu Thr Gly Leu Lys Glu Leu Asp Leu Ser Gly Phe Asp Arg Glu
                565                 570                 575
```

```
Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
            595                 600             605

Gln Ile Phe Asp Thr Met Leu Ser Thr Ile Ser Asn His Val Gly Ser
        610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
            690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
            770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
            835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
            915                 920                 925

Thr Ile Met Lys Thr Val Thr Thr Ala Lys Glu Leu Ser Gln Gln Lys
            930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975
```

-continued

```
Asn Ala Asn Ala Gly Val Leu Lys Asp Cys Ile Glu Lys Arg Gln Leu
            980                 985                 990
Leu Lys Lys
        995
```